United States Patent
Carnazzo

(10) Patent No.: US 6,294,579 B1
(45) Date of Patent: Sep. 25, 2001

(54) METHOD FOR IMPROVING DELIVERY OF TYROSINE SUPPLEMENTATION

(76) Inventor: Joseph W. Carnazzo, P.O. Box 150, Boys Town, NE (US) 68010

(*) Notice: Subject to any disclaimer, the term of this patent is extended or adjusted under 35 U.S.C. 154(b) by 0 days.

(21) Appl. No.: 09/415,808

(22) Filed: Oct. 11, 1999

(51) Int. Cl.$^7$ .................................................. A61K 31/195
(52) U.S. Cl. ............................................................. 514/567
(58) Field of Search ........................................... 514/567

(56) References Cited

U.S. PATENT DOCUMENTS

| | | |
|---|---|---|
| 4,255,438 | 3/1981 | Kane et al. . |
| 4,390,523 | 6/1983 | Huchette et al. . |
| 4,435,424 | 3/1984 | Wurtman . |
| 4,542,123 | 9/1985 | Wurtman . |
| 5,096,812 | 3/1992 | Wurtman . |
| 5,206,220 * | 4/1993 | Hilton .................................. 514/19 |
| 5,290,562 * | 3/1994 | Meybeck et al. .................. 424/450 |
| 5,767,159 | 6/1998 | Hultman et al. . |
| 5,866,537 | 2/1999 | Bianchi . |
| 5,925,378 | 7/1999 | Carnazzo . |

FOREIGN PATENT DOCUMENTS

| | | |
|---|---|---|
| 0 449 787 A2 | 10/1991 | (EP) . |
| 1357813 | 6/1979 | (GB) . |

OTHER PUBLICATIONS

Anisman, H., et al. (1980). "Copning with stress, norepinephrine depletion and escape performance, "*Brain Research* 191:583–588.
Davis, J. M. et al. (1997). "Possible mechanisms of central nervous system fatigue during exercise, " *Med. Sci. Sports Exerc.* 29(1):45–57.
Groff, J. L., et al. (1996). Advanced Nutrition and Human Metabolism (2d ed. ), West Publishing (p. 492 only).
Stone, E. A. (1971). "Hypothalamic norepinephrine after acute stress, "*Brain Research* 35:260–263.
Banderet, L. E., et al. (1989). "Treatment with Tyrosine, a Neurotransmitter Percursor, Reduces Environmental Stress in Humans," *Brain Res. Bull.* 22:759–762.
The Merck Manual on Line 284. "Neurotransmission: Major Neurotrasmitters, Major Receptors and Second Messenger Systems", 1996–1997 (Total of 13 p.).
Alonso, R., et al. (1982). "Elevation of Urinary Catecholamines and Their Metabolites Following Tyrosine Administration in Humans, "*Biological Psychiatry* 17:781–790.
Owasoyo, J. O., et al. (1992). "Tyrosine and its Potential Use as a Countermeasure to Performance Decrement in Military Sustained Operations, "*Aviation, Space, and Environmental Medicine,* pp.364–369.
Salter, C. A. (1989) "Dietary Tyrosine as an Aid to Stress Resistance Ampng Troops, " *Mititary Medicine* 154:144–146.
Wurtman, R. J. et al. (1991). "Exercise, Plasma Composition, and Neurotransmission, " *Advances in Nutrition and Top Sport Sci.* 32:94–109.
Applegate, L. (1998). "Beating the Brain Drain," *Runner's Worlds, www.runnersworld.com/nutrition/nubrainfood.html* (Total of 4 pp.).
Elwes, R. D. C., et al. "Treatment of Narcolepsy with L–Tyrosine: Double–Blind Placebo–Controlled Trial, " *The Lancet, pp. 1067–1069,* Nov. 1989.
Lehnert, H., et al. (1993). "Amino Acid Control of Neurotransmitter Synethsis and Release: Physiological and Clinical Implications," *Psychother. Psychosom.* 60:18–32.
Lou, H. C. et al. (1987). "Incerased Vigilance and Dopamine Synethsis by Large Doses of Tyrosine or Phenylalanine Restriction in Phenylketonuria, " *Acta. Paediatr.Scand.* 76:560–565.
Maddrey, W. C., et al. (1976). "Effects of kelo analogues of essential amino acids in portal–systemic encephalopathy. " *Gastroenterology* 71:190–5 (abstract only) (Total 1 p.).
Druml, W., et al. (1989). "Phenylanine and tyrosine metabolism in renal failure: dipeptides as tyrosine source, " *Kidney Int. Suppl.* 27:S282–6 (abstract only) (Total 1 p.).
Fernandez–Lopez, J. A., et al. (1992). "Rat intestinal amino acid balnaces after the adminstration of an oral protein load, " *Biochem. Int.* 26:297–308 (abstract onlt) (Total 1 p.).
Stehle, P. (1988). "Need–related availabilty of short–chain peptides—a prerequisite for their usein artifical feeding. " *Infusionstherapie* 15:27–32 (abstract only) (Total 1 p.).
Martin–DuPan, R., et al. (1982). "Effect of Various Oral Glucose Doses on Plasma Neutral Amino Acid Levels." *Metabolism* 31:937–943.
Mauron, C., et al. (1982). "Co–Administering Tyrosine with Glucose Potentiates Its Effect on Brain Tyrosine Levels. " *J. Neural Transmission* 55:317–321.
Reinstein, D. K., et al. (1985), "Dietary Tyrosine Suppresses the Rise in Plasma Corticosterone Following Acute Stress in Rats," *Life Sciences* 37:2157–2163.

(List continued on next page.)

*Primary Examiner*—Raymond Henley, III
(74) *Attorney, Agent, or Firm*—Rothwell, Figg, Ernst & Manbeck

(57) ABSTRACT

The base compound for practicing the present invention is L-tyrosine effervescent powder, granules or tablet. Soluble effervescent powders, granules and tablets are prepared by blending and/or compression and contain, in addition to active ingredients mixtures of acids (citric acid, tartaric acid) and sodium bicarbonate, which release carbon dioxide when dissolved in water. They are intended to be dissolved or dispersed in water before administration. Effervescent powders, granules and tablets should be stored in tightly closed containers or moisture-proof packs, labeled to indicate that they are not to be swallowed directly.

19 Claims, No Drawings

OTHER PUBLICATIONS

Reinstein, D. K., et al. (1984). "Tyrosine Prevents Behavioral and Neurochemical Correlates of an Acute Stress in Rats," *Life Sciences* 34:2225–2231.

Richardson, Mary Ann, Ph.D., Editor (1990). "Precursor Control of Catecholamine Metabolism," [*Chapter 1*]*Amino Acids in Psychiatric Disease*, pp. 3–29.

Sved, A. F., et al. (1979). "Tyrosine administration reduices blood pressure and enhances brain norepinephrine release in spontaneously hypertensive rats," *Prac. Natl. Acad. Sci. USA* 76:3511–3514.

Wurtman, R. J., et al. (1991). "Exercise, Plasma Composition, and Neurotransmission," *Advanced in Nutrition and Top Sport. Med. Sport Sci.* 32:94–109.

* cited by examiner

METHOD FOR IMPROVING DELIVERY OF TYROSINE SUPPLEMENTATION

BACKGROUND OF THE INVENTION

1. Technical Field

This invention relates to a method of effervescent formulation for the promotion of tyrosine or a tyrosine precursor solubility, absorption and accuracy of measure for oral supplementation and its use with vitamin, mineral and nutritional supplements.

2. Description of the Related Art

Tyrosine is the amino acid precursor for the synthesis of the neurotransmitters norepinephrine and dopamine. A number of studies have shown that stress-induced depletion of brain norepinephrine is associated with performance deficit. Tyrosine appears to have a positive impact on stress-induced performance degradation in humans.

Tyrosine is a large, neutral amino acid found in dietary proteins. It is also formed in the liver and, to a limited extent, in the brain from phenylalanine, an essential amino acid. The hydroxylation of phenylalanine by phenylalanine hydroxylase forms tyrosine which is the precursor for the biosynthesis of the catecholamine neurotransmitters dopamine and norepinephrine. The recommended daily intake of phenylalanine is 2.2 grams. Tyrosine is found in both animal and vegetable protein with the level of tyrosine found in human food varying widely. Thus the total daily intake of tyrosine by an individual would vary according to the combination of animal and vegetable protein ingested.

The fundamental structural units of proteins are α-aminoacids, about 20 of which participate prominently in protein formation. These building-block molecules contain at least one carboxyl group and one α-amino group, but differ in the structure of the remainder of the molecule. All except the simplest one, glycine, are capable of existing in both D and L configurations with respect to their α-carbon but proteins contain only the L-enantiomers. The actual protein molecule consists of long-chain polymers which may be looked upon as having resulted from condensation of the amino acids thus producing amide (commonly called peptide) linkages. The number of amino acid molecules so condensed varies widely among different proteins, ranging from perhaps as few as 30 up to tens of thousands. Proteins are thus macromolecules which differ primarily from each other in the number of amino acid residues present and in the sequence of these in the polymer chain.

A neurotransmitter (NT) is defined as a chemical that is selectively released from a nerve terminal by an action potential, interacts with a specific receptor on an adjacent structure, and elicits a specific physiologic response. Most NTs derive from amino acids (or related compounds such as choline). Certain neurons synthesize only one, neuron-specific NT, others have been shown to synthesize 2 neurons or more NTs. Some neurons modify amino acids to form the "amine" transmitters (e.g., norepinephrine, serotonin); others combine amino acids to form "peptide" transmitters (e.g., endorphins, enkephalins); and still other neurons use amino acids unchanged or synthesized as transmitters. A few NTs are not related to amino acids.

Dopamine (DA) is the NT of some peripheral nerve fibers and of many central neurons (e.g., substantia nigra, midbrain, hypothalamus). The amino acid tryosine is taken up by dopaminergic neurons, converted by the enzyme tyrosine hydroxylase to 3,4-dihydroxyphenylalanine (dopa), decarboxylated by the enzyme aromatic L-amino acid decarboxylase to DA, and stored in vesicles. After release, DA interacts with dopaminergic receptors and is then pumped back by active processes (re-uptake) into the prejunctional neurons. DA levels are held constant by changes in tyrosine hydroxylase activity and the enzyme monoamine oxidase (MAO), which is localized in nerve terminals and metabolizes dopamine. DA is metabolized to several metabolites, including specifically homovanillic acid.

Norepinephrine (NE) is the NT of most postganglionic sympathetic fibers and many central neurons (e.g., locus ceruleus, hypothalamus). NE synthesis, like that of DA, also starts with the precursor tyrosine but continues as DA is hydroxylated by dopamine-beta-hydroxylase to form NE, which is stored in vesicles. Upon release, NE interacts with adrenergic receptors. This action is terminated largely by the re-uptake of NE back into the prejunctional neurons. Tyrosine hydroxylase and MAO regulate intraneuronal NE levels. Metabolism of NE occurs via MAO and catechol-O-methyltransferase to inactive metabolites (e.g., normetanephrine, 3-methoxy-4-hydroxyphenylethylene glycol, 3-methoxy-4-hydroxymandelic acid).

One of the factors which limits the extent of resistance the individual can mount apparently is his capacity to produce and respond to the neurotransmitter norepinephrine (NE). Studies with both animals and humans reveal that stress causes a sharp increase in the brain's use of NE because NE tracts are those activated by stress. This surge in use of NE tends to deplete available supplies, and as neural stores decline, so does the capacity to continue normal levels of performance. That the loss of NE is the cause and not merely the correlate of stress-induced behavioral decrements is suggested by the finding that biochemical reduction of NE even in the absence of stress can cause a reduction in performance similar to that caused by stress alone.

Tyrosine must compete with all the other large neutral amino acids for transport across the blood brain barrier. Therefore, the ratio of tyrosine to its amino acid competitors determines its rate of entry into the brain. Once in the brain, more is converted into NE if the neural circuits which require NE are activated. In other words, when the organism is at rest, excess tyrosine is not converted into a larger reserve pool of NE. But when the individual is under stress, available tyrosine is converted into NE at a faster rate to replenish expended NE. If sufficient tyrosine is not available to replace that which is used, NE and performance continue to decline.

This dietary-biochemical-neural pathway suggests a novel approach to slowing stress-induced performance degradation. If stress uses NE and NE decline reduces the level of functioning and performance, NE levels and performance can be restored by additional amounts of NE's precursor tyrosine.

A tyrosine dietary supplement is a realistic alternative to increasing NE levels for slowing stress-induced performance degradation. L-tyrosine is the most commonly used tyrosine supplement for oral consumption, although other tyrosine salts, tyrosine isomers, and synthetic tyrosine formulations exist. L-tyrosine supplementation of 100 mg/kg to 150 mg/kg were the most commonly used dosages in human studies. These dosages created maximal increases that were seen for 2 hours after tyrosine ingestion, thereafter catecholamine levels returned to base line. Supplemental tyrosine (100 mg/kg) has, in fact, been shown to enhance mental performance, improve mood, and diminish symptoms in human subjects exposed to such stressors as cold and high altitude. To achieve desired effects dosages of 7 to 15 grams of L-tyrosine will need to be consumed 1 hour prior to competition or intense exercise.

The problem with existing tyrosine supplements is that accurate dosage is difficult to achieve. This is so because tyrosine does not dissolve well in water or other neutral pH liquids and is very acid liable. This results in irregular dosage, inconsistent results, and limited absorption due to stomach acid destruction.

SUMMARY OF THE INVENTION

This method of promoting delivery of tyrosine, preferably a supplement of L-tyrosine or N-acetyl tyrosine, to the human body includes formation of tyrosine in an effervescent form which allows the tyrosine to dissolve and disperse into solution upon activation with water. The increase in solubility and dispersal gives a more uniform absorption of the product after ingestion. The effervescent form of tyrosine will buffer stomach acid, thus inhibiting stomach acid destruction of tyrosine after consumption. Because the tyrosine is in an effervescent powder packet, effervescent granule packet or tablet form, it offers a more accurate form of administration than bulk powders or suspensions. Tyrosine is soluble in alkaline solutions but does not readily dissolve in water or other neutral pH liquids. The effervescent form of tyrosine having an alkaline pH makes the tyrosine much more soluble in the liquid form. The use of flavorings in the effervescent method to deliver tyrosine is to be used to increase to palatability of the products.

It is therefore a general object of the present invention to provide a method of delivering a precise amount of tyrosine oral supplement to the human body.

It is another object of the invention to provide a tyrosine supplement that is more readily soluble and provides consistent results.

Still another object of the invention is to provide a tyrosine oral supplement that can be combined with other vitamins, minerals, and supplements for enhancement of health, nutrition, and related goals.

These and other objects will be obvious to those skilled in the art.

DESCRIPTION OF THE PREFERRED EMBODIMENT

The inventor has discovered that tyrosine may be uniformly and accurately dispensed when completely dissolved and dispersed in liquid. More specifically, the tyrosine has been created in the form of an effervescent in tablet or particulate form which increases the pH of water to thereby increase the solubility of the tyrosine in the liquid.

L-tyrosine and N-acetyl tyrosine, as used in the prior art, do not readily dissolve in water or other neutral pH liquids. The combination of tyrosine and other chemicals to create an effervescent which, when combined with a proper measure of water, creates a liquid having an alkaline pH, making the tyrosine much more soluble in the liquid. The increase in solubility allows for more uniform absorption of the tyrosine after ingestion.

In addition, because the tyrosine is packaged in either tablet or premeasured particulate form, a precise amount of the compound is ingested. The prior art bulk powder form required the consumer to measure the proper amount of the product and dissolve the product in water. The precision of such measurement is uncertain. Furthermore, because prior art formulations of tyrosine required dissolution of tyrosine in a neutral pH liquid, non-uniform amounts of the tyrosine supplements are commonly undissolved and subsequently not ingested by the consumer. The result is non-uniform dosages and ingestion at non-uniform rates.

The use of a pre-measured effervescent assures complete dissolution and dispersal of the tyrosine and uniform rates of ingestion of the same. These goals are achieved by virtue of increasing the pH of the liquid and the agitation provided by the effervescence of the compound. The soluble effervescent will contain a mixture of acids, bicarbonates, and other agents which release carbon dioxide when dissolved in water.

The chemical formula for tyrosine is $C_9H_{11}NO_3$, and has a molecular weight of 181.19. Tyrosine is a dietary amino acid. In addition to its value as an energy substrate and in protein synthesis, it is a precursor to numerous biogenic amines and neurotransmitters.

Previously, tyrosine's use has been limited by its relative insolubility in water and susceptibility to stomach acid destruction. The use of effervescent technology, therefore, is employed to alter the pH of the water, giving tyrosine greater solubility in water and buffering stomach acid to limit tyrosine destruction.

The method of the present invention relies upon the combination of tyrosine with an effervescent to create an alkaline solution which is ingested by the consumer. The effervescent raises the pH to form an alkaline solution, whereby the tyrosine will uniformly dissolve and completely disperse in solution. In its preferred form, the invention includes a soluble effervescent containing tyrosine, at least one acid, and at least one bicarbonate for releasing carbon dioxide when dissolved in a neutral pH liquid, such as water. In the most preferred form of the invention, L-tyrosine or N-acetyl tyrosine is the type of tyrosine that is utilized.

The effervescent ingredients preferably utilize a mixture of acids, including citric acid and tartaric acid. Sodium bicarbonate or potassium bicarbonate may be utilized for the release of carbon dioxide. In addition, starch, flavoring agents, and lubricants for tablet compression are also utilized in the effervescent tablet. While the effervescent is preferably in the form of a tablet, it may also be utilized in a particulate form. The effervescent must be stored in a sealed container or other moisture-proof package, since water or other liquids will activate the effervescent. This also allows for a method of premeasuring the tyrosine dosage.

The effervescents are not to be swallowed directly, since they release carbon dioxide as they dissolve. Thus, the initial step in the method of the invention is to open the moisture-proof package containing the effervescent and dispense it into a container of water or other pH neutral liquid. Once the effervescent tyrosine has been dissolved and dispersed, the solution should be ingested immediately.

Thus, it can be seen that the invention accomplishes at least all of its stated objectives.

I claim:

1. A method of promoting delivery of tyrosine supplementation into a human body, comprising the steps of:

dispensing a combination of an effervescent and a predetermined amount of tyrosine into a neutral pH liquid;

dissolving the combination substantially in the liquid; and a human ingesting the liquid.

2. The method of claim 1 wherein the dispensing step includes the initial step of opening a moisture-proof package containing the combination.

3. The method of claim 2 wherein the combination is in the form of a tablet.

4. The method of claim 2 wherein the combination is in the form of a premeasured particulate.

5. The method of claim 3 wherein the dispensing step includes dispensing the tablet in water.

6. The method of claim 4 wherein the dispensing step includes dispensing the particulate in water.

7. The method of claim 1 wherein the dispensing step includes dispensing the combination in water and the dissolving step includes the formation of an alkaline solution.

8. The method of claim 1 wherein the ingestive step is performed approximately one hour prior to assumption of vigorous activity by the human.

9. The method of claim 1 wherein the tyrosine is replaced by a tyrosine precursor.

10. The method of claim 9 wherein the tyrosine precursor is phenylalanine.

11. The method of claim 1 wherein the tyrosine is synthetic tyrosine.

12. In combination:
   an effervescent; and
   tyrosine mixed with the effervescent in an amount effective to enhance the solubility of the tyrosine in a pH neutral liquid and to enhance the rate of tyrosine absorption in a human when the human ingests the effervescent/tyrosine/liquid solution.

13. The combination of claim 12 wherein the effervescent is in the form of a tablet.

14. The combination of claim 12 wherein the effervescent is in the form of a particulate.

15. The combination of claim 12 wherein the effervescent includes an acid and a bicarbonate.

16. The combination of claim 15 wherein the acid is selected from the group consisting of citric acid and tartaric acid.

17. The combination of claim 15 wherein the bicarbonate is selected from the group consisting of sodium bicarbonate and potassium bicarbonate.

18. The combination of claim 12 comprising an effervescent tablet including:
   Tyrosine 0.5 grams–6 grams
   Citric Acid 1 grams–12 grams
   Sodium Bicarbonate 0.6 grams–7.2 grams; and
   Potassium Bicarbonate 0.4 grams–3.6 grams.

19. The combination of claim 18 comprising an effervescent tablet including:
   Tyrosine 500 mg;
   Citric Acid 100 mg;
   Sodium Bicarbonate 600 mg;
   Potassium Bicarbonate 400 mg;
   Sorbitol/Mannitol 850 mg;
   Fruit Flavor 150 mg;
   Aspartame 35 mg;
   Mineral Oil 35 mg; and
   Sodium Lauryl Sulfate 8 mg.

* * * * *